(12) United States Patent
Mabkhot et al.

(10) Patent No.: US 10,071,960 B1
(45) Date of Patent: Sep. 11, 2018

(54) ENAMINONE-GRAFTED TRITHIOCARBONATE WITH ANTICANCER AND ANTIMICROBIAL ACTIVITY

(71) Applicant: KING SAUD UNIVERSITY, Riyadh (SA)

(72) Inventors: Yahia Nasser Mabkhot, Riyadh (SA); Jamal Mohammed Ali Khaled, Riyadh (SA); Mujeeb Abdullah Sultan, Riyadh (SA); Fahd Ali Nasr Mohammed, Riyadh (SA); Naiyf Sultan Helial Alaloi Alharbi, Riyadh (SA); Salim Showiman Al-Showiman, Riyadh (SA); Hazem Ahmed Ghabbour, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/726,263

(22) Filed: Oct. 5, 2017

(51) Int. Cl.
*C07C 329/06* (2006.01)

(52) U.S. Cl.
CPC .................................. *C07C 329/06* (2013.01)

(58) Field of Classification Search
None
See application file for complete search history.

(56) References Cited

U.S. PATENT DOCUMENTS

| | | |
|---|---|---|
| 3,689,517 A | 9/1972 | Carriel |
| 5,288,753 A | 2/1994 | Green, II |
| 5,360,782 A | 11/1994 | Young |
| 5,530,116 A | 6/1996 | Demuth, Jr. |
| 5,656,623 A | 8/1997 | White |

FOREIGN PATENT DOCUMENTS

CN        103910644        7/2014

OTHER PUBLICATIONS

Bunyatova et al., "Synthesis and Characterization of Trithiocarbonate-Organoclays Nanohybrids and Their Interaction with MCF-7 Cancer Cells", J. Chem. Chem. Eng. (2014), pp. 1068-1081, vol. 8.
Riyadh, Sayed M., "Enaminones as Building Blocks for the Synthesis of Substituted {Pyrazoles with Antitumor and Antimicrobial Activities", Molecules (2011), pp. 1834-1853, vol. 16.

*Primary Examiner* — Samantha L Shterengarts
(74) *Attorney, Agent, or Firm* — Richard C. Litman (57) ABSTRACT

The present subject matter is directed to an enaminone-grafted trithiocarbonate compound having the structure:

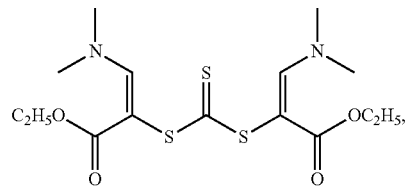

and the anticancer and antimicrobial activities exhibited by the compound.

15 Claims, 6 Drawing Sheets

ENAMINONE-GRAFTED TRITHIOCARBONATE WITH ANTICANCER AND ANTIMICROBIAL ACTIVITY

TECHNICAL FIELD

The disclosure of the present patent application relates to anticancer and antimicrobial agents, and particularly to an enaminone-grafted trithiocarbonate derivative.

BACKGROUND

Cancer remains the leading cause of death around the world. In 2012, approximately 8.2 million deaths were attributed to cancer, and there were 14.1 million new cases of cancer reported globally. Current cancer treatment options have several serious side effects. According to the U.S. National Cancer Institute, common side effects of cancer treatment include pain, anemia, loss of appetite, constipation, diarrhea, urinary issues, edema, nausea and vomiting, mouth and throat problems, bleeding and bruising, delirium, problems with memory and concentration, nerve problems, fatigue, hair loss, infection and neutropenia, lymphedema, sexual fertility problems, and sleep problems.

Because of the serious side effects of anticancer chemotherapeutic agents, pharmaceutical companies, medicinal chemists, and other health professionals and researchers recognize there is an urgent need to discover and develop new compounds for use as anticancer agents with safer side effects.

SUMMARY

The present subject matter is directed to an enaminone-grafted trithiocarbonate derivative, and its uses as a potent anticancer agent and an antimicrobial agent.

The enaminone-grafted trithiocarbonate derivative can be (Z)-ethyl 3-(dimethylamino)-2-(((((Z)-1-(dimethylamino)-3-ethoxy-3-oxoprop-1-en-2-yl)thio)carbonothioyl)thio) acrylate (compound 3), having the following structure:

An embodiment of the present subject matter is directed to a method of synthesizing the enaminone-grafted trithiocarbonate compound, comprising mixing 2,2'-(thiocarbonyl-bis(sulfanediyl))diacetate with N,N'-dimethylormamide dimethyl acetal (DMF-DMA) to form a mixture, heating the mixture to at least about 100° C. for at least about one hour to form a heated mixture including the enaminone-grafted trithiocarbonate compound, allowing the heated mixture to cool to room temperature to form a cooled mixture, d) maintaining the cooled mixture for at least about 8-10 hours to form a maintained mixture; and e) isolating the enaminone-grafted trithiocarbonate compound from the maintained mixture.

An embodiment of the present subject matter is directed to a method of treating a disease comprising administering an effective amount of the compound of the present subject matter to a patient afflicted by the disease.

These and other features of the present disclosure will become readily apparent upon further review of the following specification and drawings.

BRIEF DESCRIPTION OF THE DRAWINGS

FIGS. 8A and 8D are vehicle (control); FIGS. 8B and 8E reflect treatment with 50 μg/ml; FIGS. 8C and 8F reflect treatment with 100 μg/ml.

Similar reference characters denote corresponding features consistently throughout the attached drawings.

DETAILED DESCRIPTION

An enaminone-grafted trithiocarbonate derivative can include (Z)-ethyl 3-(dimethylamino)-2-(((((Z)-1-(dimethylamino)-3-ethoxy-3-oxoprop-1-en-2-yl)thio)carbonothioyl) thio)acrylate 3, having the following structural formula:

In an embodiment, the enaminone-grafted trithiocarbonate derivative is an anticancer agent. In an embodiment, the enaminone-grafted trithiocarbonate derivative is an antimicrobial agent.

An embodiment of the present subject matter is directed to a method of synthesizing an enaminone-grafted trithiocarbonate derivative compound comprising: mixing 2,2'-(thiocarbonylbis(sulfanediyl))diacetate with N,N'-dimethylformamide dimethyl acetal (DMF-DMA) to form a mixture, heating the mixture to at least about 100° C. for at least about one hour to form a heated mixture including the enaminone-grafted trithiocarbonate compound, allowing the heated mixture to cool to room temperature to form a cooled mixture, maintaining the cooled mixture for at least about 8-10 hours to form a maintained mixture; and isolating the enaminone-grafted trithiocarbonate derivative compound from the maintained mixture.

In an embodiment, the isolated enaminone-grafted trithiocarbonate derivative is in crystal form.

In an embodiment, the method further comprises a preliminary step of reacting ethyl cyanoacetate, carbon disulfide ($CS_2$), and ethyl 2-chloroacetate to synthesize the diethyl 2,2'-(thiocarbonylbis(sulfanediyl))diacetate.

An embodiment of the present subject matter is directed to a method of treating a disease comprising administering a therapeutically effective amount of the enaminone-grafted trithiocarbonate derivative to a patient afflicted by the disease. In an embodiment, the disease comprises cancer. The cancer may be liver cancer, colon cancer, or breast cancer. In an embodiment, the disease is a fungal infection, which may be caused by a yeast or mold. In an embodiment, the disease is caused by bacteria, such as a gram positive bacteria or gram negative bacteria.

Figure 1:
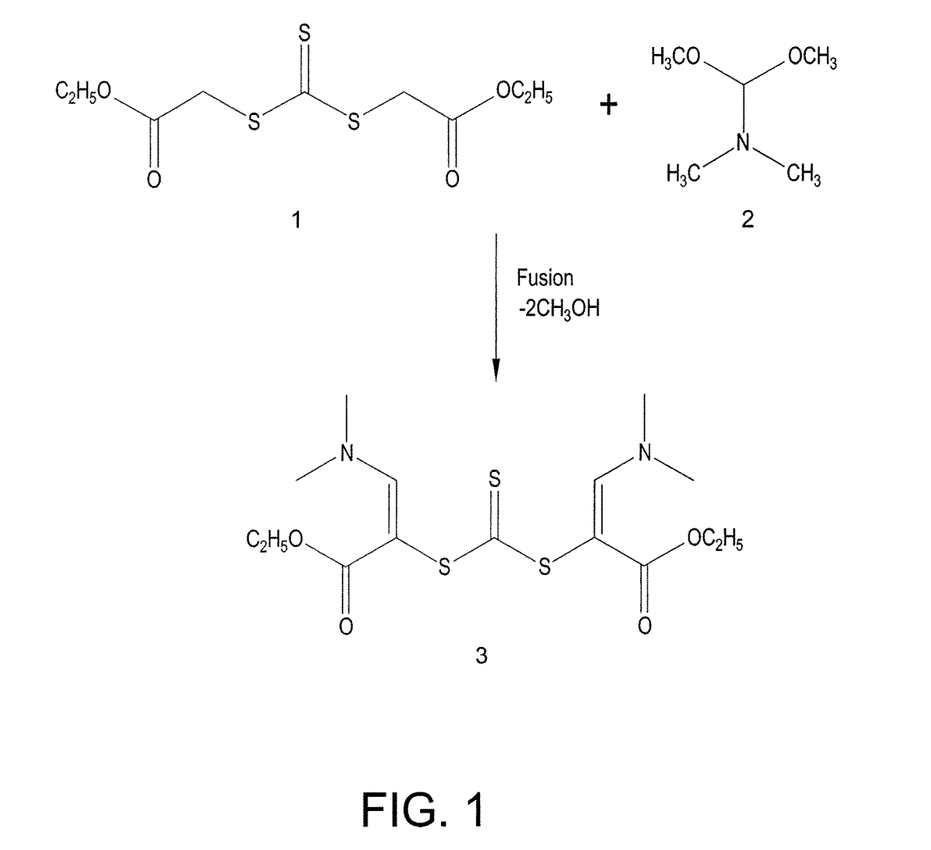
FIG. 1 is a reaction scheme for synthesizing the enaminone-grafted trithiocarbonate described herein.

As stated above, diethyl 2,2'-(thiocarbonylbis(sulfanediyl))diacetate (compound 1) can be prepared according to a preliminary synthetic route involving reacting ethyl cyanoacetate, carbon disulfide ($CS_2$), and ethyl 2-chloroacetate. Referring to the reaction scheme of FIG. 1, a mixture of (compound 1) and DMF-DMA (compound 2) can be fused at about 100° C. for about 1 hour to provide (Z)-ethyl 3-(dimethylamino)-2-(((((Z)-1-(dimethylamino)-3-ethoxy-3-oxoprop-1-en-2-yl)thio)carbonothioyl)thio)acrylate (compound 3) as a crystal after keeping the mixture at room temperature overnight or for at least about 8-10 hours.

The synthesized trithiocarbonate compound 3 was characterized by spectroscopic techniques of IR, $^1$H-NMR, $^{13}$C-NMR, and HRMS, and its 3D structure was further identified by X-ray single crystallography. In IR spectrum, the enaminone group, an important characteristic absorption of compound 3, appeared at ν 1686 and 1613 cm$^{-1}$. The $^1$H-NMR and $^{13}$C-NMR spectra of compound 3 showed symmetric pattern in CDCl$_3$ and was slightly different in DMSO. The triplet signal at δ 1.05 ppm with coupling constants J=7 Hz is integrated for the protons assigned for methyl group (—OCH$_2$CH$_3$) while the signal of protons assigned to methylene group (—OCH$_2$CH$_3$) appeared as a quartet at δ 3.94 ppm with coupling constants J=7 Hz. The singlet signals at δ 3.13, 3.28, and 3.94 ppm are integrated for the protons assigned for methyl groups attached to nitrogen atom (N—CH$_3$). The signal of olefinic proton (N—CH═C), the characteristic signal of the product 3 when compared to its precursor 1, appeared as a singlet at δ 8.01 ppm. In the $^{13}$C-NMR spectrum, the methyl groups appeared at δ 14.99 ppm, while methylene groups appeared at δ 60.14 ppm. The peaks which appeared at δ 81.85, 156.04, and 167.4 ppm are due to (S—C═CHN—), (C═CH—N—), and (—C═O—), respectively. The thiocarbonyl peak (—S—C═S—S) of product 3 was downshifted more and appeared at δ 233.39 ppm; however, this group appeared at δ 220.2 ppm in the precursor 1, and the shifting may be attributed to the new incorporated enaminone.

Figure 2:
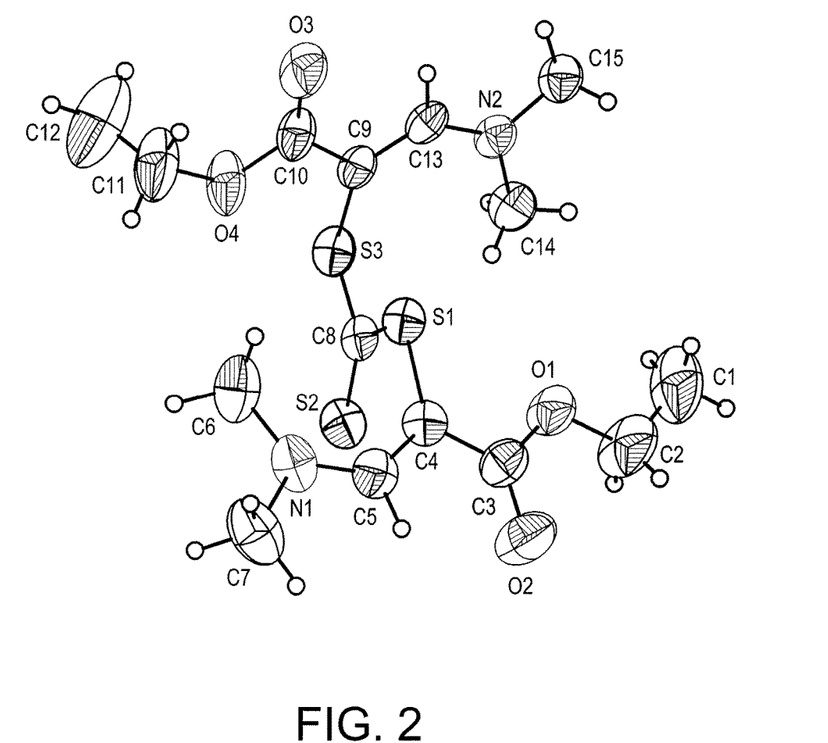
FIG. 2 is an ORTEP diagram of the compound 3. Displacement ellipsoids are plotted at the 40% probability level for non-H atoms.
Figure 3:
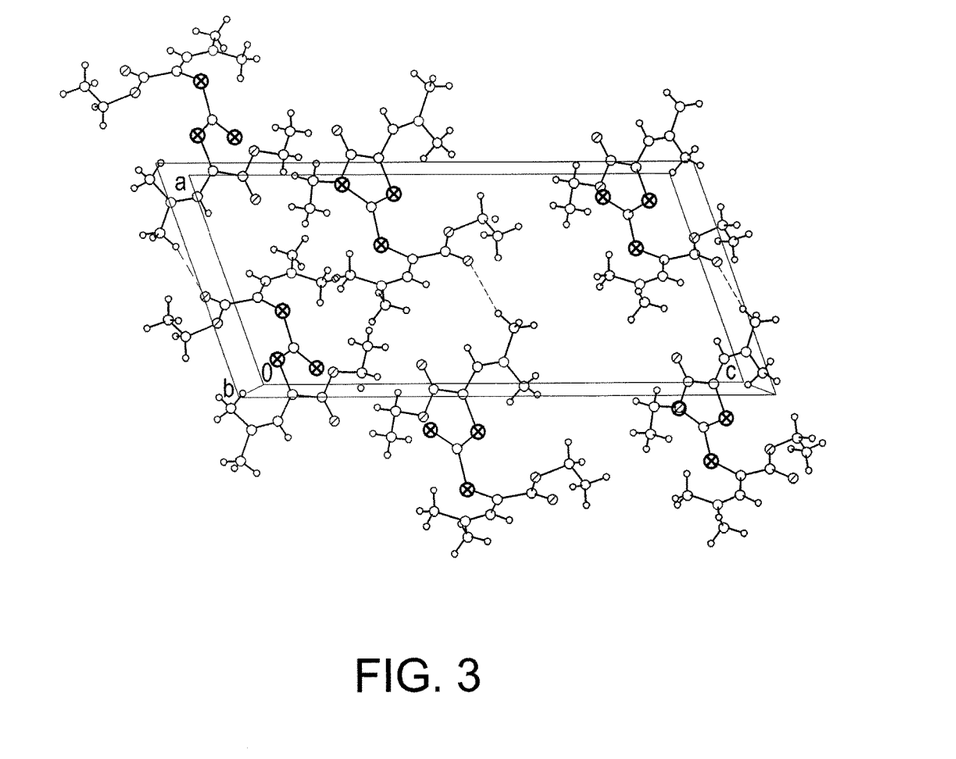
FIG. 3 shows the molecular packing of compound 3. Viewed hydrogen bonds are drawn as dashed lines along the a axis.

The x-ray single diffraction analysis clarified the 3D structure of compound 3. In the molecular structure of compound 3, $C_{15}H_{24}N_2O_4S_3$, was crystallized in the Monoclinic, P2$_1$/c, a=10.6328 (7) Å, b=8.8416 (5) Å, c=22.8271 (13) Å, β=109.309 (5°), V=2025.3 (2) Å$^3$, Z=4. Details of crystallographic data and refinement information of compound 3 are summarized in Table 1, while selected bond lengths and bond angles are listed in Table 2. Further, the asymmetric unit containing one independent molecule is shown in FIG. 2. All bond lengths and angles are in normal ranges. In the crystal packing (shown in FIG. 3), molecules are linked via two intermolecular hydrogen bonds (shown in Table 3).

TABLE 1

Experimental Data of Compound 3

| Crystal data | |
|---|---|
| Chemical formula | $C_{15}H_{24}N_2O_4S_3$ |
| Mr | 392.54 |
| Crystal system, space group | Monoclinic, P2$_1$/c |
| Temperature (K) | 293 |
| a, b, c (Å) | 10.6328 (7), 8.8416 (5), 22.8271 (13) |
| β (°) | 109.309 (5) |
| V (Å3) | 2025.3 (2) |
| Z | 4 |
| Radiation type | Kα |
| μ (mm$^{-1}$) | 3.52 |
| Crystal size (mm) | 0.45 × 0.41 × 0.37 |
| Data collection | |
| Diffractometer | Bruker APEX-II D8 venture diffractometer |
| Absorption correction | Multi-scan SADABS Bruker 2014 |
| Tmin, Tmax | 0.301, 0.356 |
| No. of measured, independent and observed [I > 2σ(I)] reflections | 15351, 3446, 2093 |
| R$_{int}$ | 0.086 |
| Refinement | |
| R[F$^2$ > 2σ(F$^2$)], wR(F$^2$), S | 0.066, 0.198, 1.03 |
| No. of reflections | 3446 |
| No. of parameters | 224 |
| No. of restraints | 1 |
| H-atom treatment | H atoms treated by a mixture of independent and constrained refinement |
| Δρ$_{max}$, Δρ$_{min}$ (e Å$^{-3}$) | 0.33, −0.30 |

TABLE 2

Selected Geometric Parameters (Å, °)

| S1—C4 | 1.728 (6) |
|---|---|
| S1—C8 | 1.730 (4) |
| S2—C8 | 1.630 (5) |

TABLE 2-continued

Selected Geometric Parameters (Å, °)

| | |
|---|---|
| S3—C8 | 1.750 (6) |
| S3—C9 | 1.744 (5) |
| O1—C2 | 1.455 (11) |
| O1—C3 | 1.341 (9) |
| O2—C3 | 1.205 (10) |
| O3—C10 | 1.209 (7) |
| C4—S1—C8 | 103.4 (3) |
| C8—S3—C9 | 105.8 (2) |
| C2—O1—C3 | 114.9 (7) |
| C10—O4—C11 | 117.8 (5) |
| C5—N1—C6 | 124.7 (6) |
| C5—N1—C7 | 120.1 (6) |
| C6—N1—C7 | 115.1 (5) |
| C13—N2—C14 | 124.9 (5) |
| C13—N2—C15 | 120.1 (4) |
| C14—N2—C15 | 114.8 (4) |
| O1—C2—C1 | 109.6 (9) |
| O1—C3—O2 | 122.6 (6) |
| O1—C3—C4 | 112.4 (7) |
| O2—C3—C4 | 125.0 (7) |
| O4—C10 | 1.346 (8) |
| O4—C11 | 1.491 (7) |
| N1—C5 | 1.321 (8) |
| N1—C6 | 1.440 (10) |
| N1—C7 | 1.454 (9) |
| N2—C13 | 1.332 (6) |
| N2—C14 | 1.450 (7) |
| N2—C15 | 1.443 (8) |
| S1—C4—C3 | 119.6 (5) |
| S1—C4—C5 | 125.9 (4) |
| N1—C5—C4 | 133.6 (6) |
| S1—C8—S2 | 127.4 (3) |
| S1—C8—S3 | 114.7 (3) |
| S2—C8—S3 | 117.9 (3) |
| S3—C9—C10 | 119.3 (4) |
| S3—C9—C13 | 126.1 (3) |
| O3—C10—O4 | 122.3 (4) |
| O3—C10—C9 | 125.6 (6) |
| O4—C10—C9 | 112.1 (5) |
| O4—C11—C12 | 107.6 (8) |
| N2—C13—C9 | 132.7 (5) |

TABLE 3

Hydrogen-Bond Geometry (Å, °)

| D—H⋯A | D—H | H⋯A | D⋯A | D—H⋯A |
|---|---|---|---|---|
| C7—H7A⋯O3$^i$ | 0.9600 | 2.5700 | 3.461 (9) | 155.00 |
| C13—H13A⋯O3$^{ii}$ | 0.9300 | 2.5900 | 3.462 (7) | 156.00 |

Symmetry codes: (i) x + 1, y, z; (ii) -x - 3, -y - 1, -z.

The design and synthesis of new trithiocarbonate derivatives is appealing due to the versatile applications of trithiocarbonate derivatives. The atom-efficient transformation toward the synthesis of bulk molecules from smaller starting materials is particularly desirable in organic synthesis. Further, the incorporation of a special functional group such as an enaminone group with the conjugated system NC=C—C=O in the molecules provides stability. The incorporation also provides new approaches for uses in organic synthesis, particularly for hetero pharmaceutical agents such as anti-inflammatory, antitumor, antioxidant, antibacterial, and anti-tuberculosis agents. In this context, N,N'-dimethylformamide dimethyl acetal (DMF-DMA) is a reagent useful in functional group transformations and in building carbon skeletons as a one-carbon synthon.

In addition, antimicrobial, chemically-synthesized agents have been widely regarded as a promising solution to combat antimicrobial resistant microbes. Organic trithiocarbonates and their derivatives are considered biological toxicants having several industrial, chemical, and medicinal applications, and many scientific researchers have confirmed trithiocarbonates have noticeable biological activity against pathogenic microbes.

Figure 4:
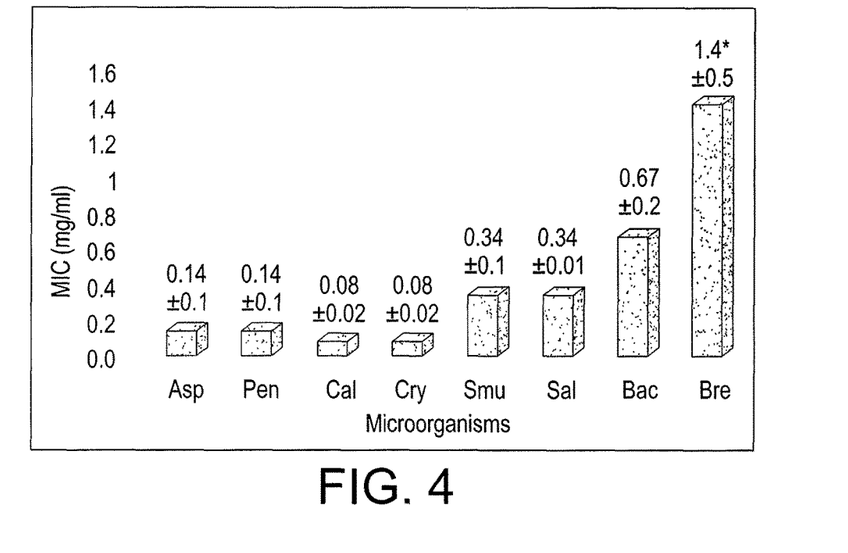
FIG. 4 is a chart of the mean±std of minimal inhibitory concentrations (MIC) of compound 3. Asp=*Aspergillus fumigatus* AUMC 8794, Pen=*Penicillium chrysogenum* AUMC 9476, Cal=*Candida albicans* ATCC 60193, Cry=*Cryptococcus neoformans* Wild strain, Smu=*Streptococcus mutans* ATCC 35668, Sal=*Salmonella typhi* Wild strain, Bac=*Bacillus subtilis*, and Bre=*Brevibacillus laterosporus* Wild strain.
Figure 5:
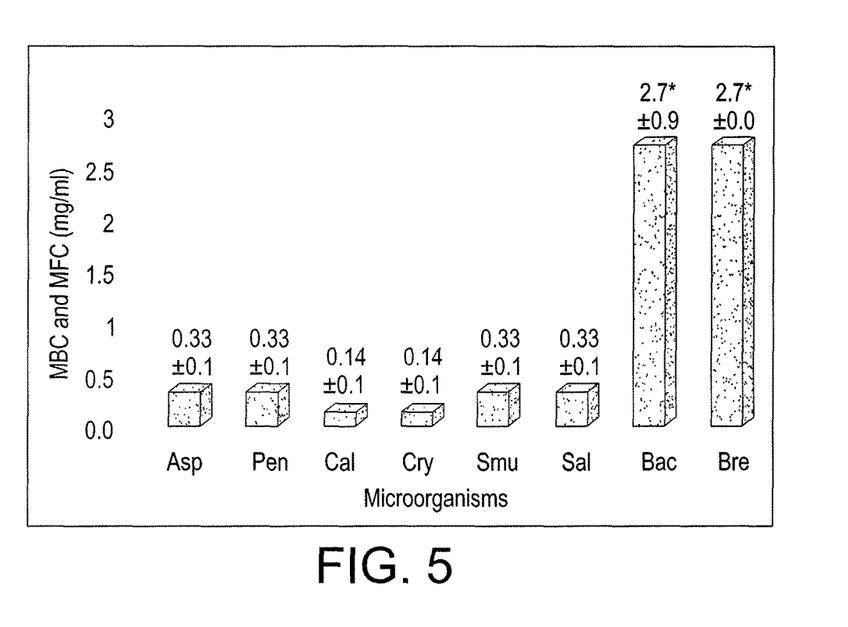
FIG. 5 is a chart of the mean±std of minimal bactericidal and minimal fungicidal concentration (MBC and MFC). Asp=*Aspergillus fumigatus* AUMC 8794, Pen=*Penicillium chrysogenum* AUMC 9476, Cal=*Candida albicans* ATCC 60193, Cry=*Cryptococcus neoformans* Wild strain, Smu=*Streptococcus mutans* ATCC 35668, Sal=*Salmonella typhi* Wild strain, Bac=*Bacillus subtilis* and Bre=*Brevibacillus laterosporus* Wild strain.

As described in detail below, present compound 3 demonstrated biological activity against Gram positive and negative bacteria, as well as yeasts and molds. MIC, MBC and MFC indicated that Bacillus subtilis and Brevibacillus laterosporus (both Gram positive bacteria) were resistant to compound 3, as compared to other tested microorganisms (FIGS. 4 and 5). As shown in FIGS. 4 and 5, the tested pathogenic yeasts (C. albicans and Cr. neformans) were more susceptible to compound 3, as compared to other tested microbes. Generally, compound 3 showed more biological activity against the yeasts and molds (fungi) than the bacteria, which may be due to compound 3 acting as a bacterial and fungal β-carbonic anhydrase inhibitor.

Recent reports have shown that carbonic anhydrase inhibitors have novel therapeutic applications. In particular, carbonic anhydrases catalyze a simple, fundamental reaction, namely $CO_2$ hydration to yield bicarbonate and protons. In many organisms, an inhibition or activation of those enzymes leads to various therapeutic applications, and α-, β-, and γ-carbonic anhydrases are detected in parasites belonging to numerous kingdoms. For instance, bacteria possess carbonic anhydrases of all classes, molds and yeast possess α- and β-, and protozoans have only α-carbonic anhydrases. Several trithiocarbonate derivatives act as microbial inhibitors, such as nickel trithiocarbonate compounds, oligomeric thiocarbonates, and an aqueous solution comprising a thiocarbonate, a sulfide, and an ammoniacal compound. Further, studies have confirmed that certain enaminone-based heterocyclic compounds have high biological activity as antimicrobial agents. In addition, various cyclic enaminone esters previously synthesized did not exhibit any significant antibacterial activity. The present inventors have discovered that compound 3, surprisingly, demonstrates significant biological activity as both an antifungal and antibacterial agent.

Figure 6:
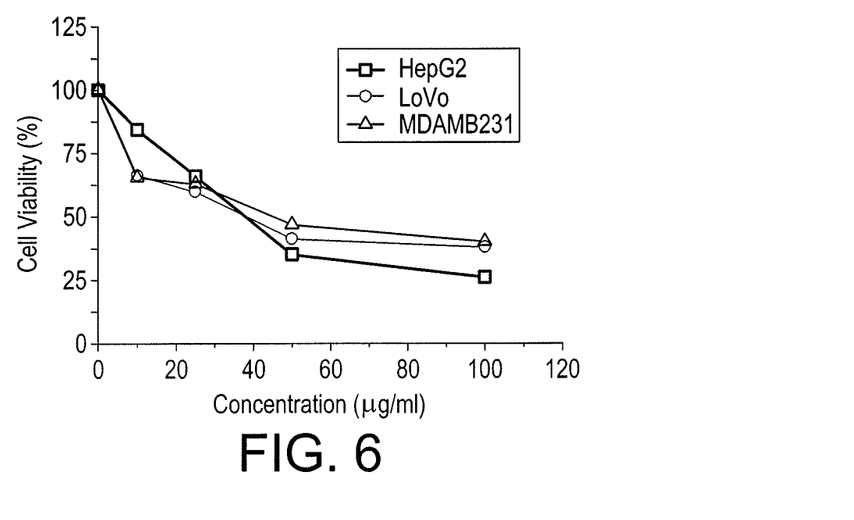
FIG. 6 is a dose responsive curve for compound 3 on three types of cells, namely human liver (HepG2), colon (LoVo), and breast (MDA-MB-231) cancer cells.
Figure 7:
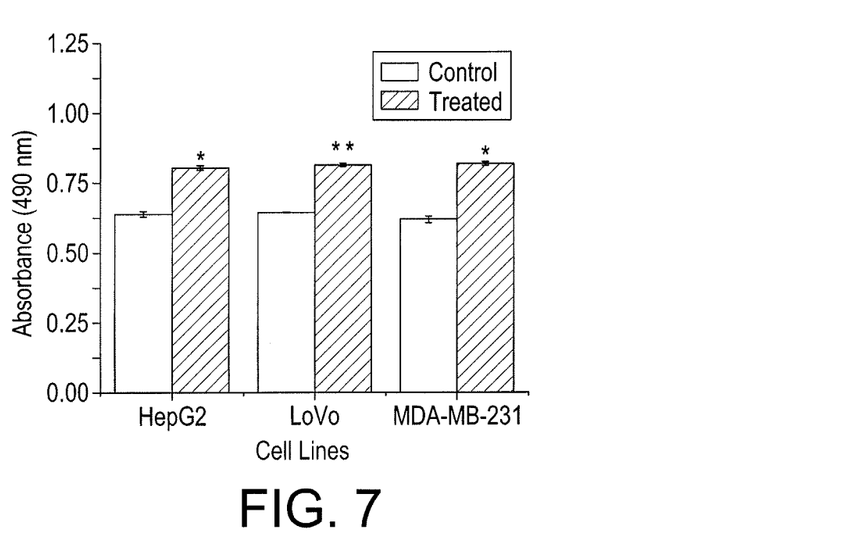
FIG. 7 is a chart showing the cytotoxic effect of compound 3 on human liver (HepG2), colon (LoVo) and breast (MDA-MB-231) cancer cells. Cells were treated with IC50 for 48 hours, and LDH released into media was determined at 490 nm in an ELISA reader. Statistical differences were analyzed with Student's t-test. Data represent the mean±S.D. (*P<0.05, **P<0.001 were significant compared to control) of three independent experiments carried out in triplicates.
Figure 8A:
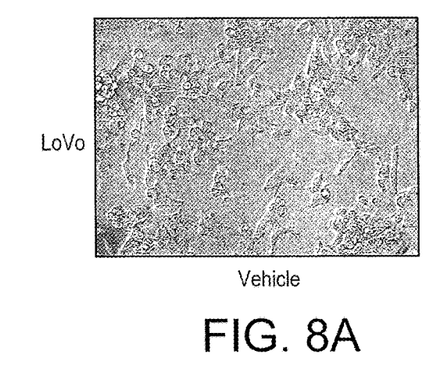
FIGS. 8A, 8B, and 8C show images of cytotoxic and morphological changes in LoVo.
Figure 8B:
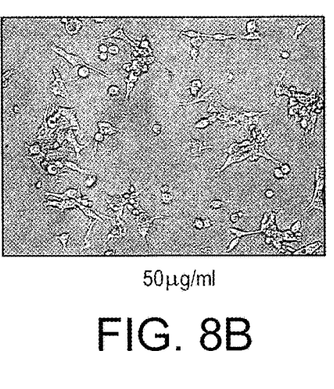
Figure 8C:
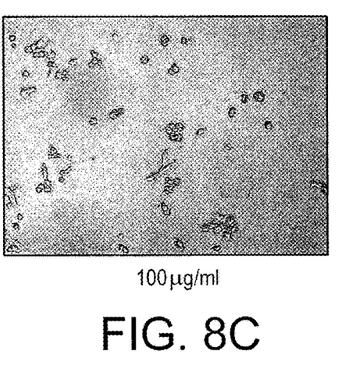
Figure 8D:
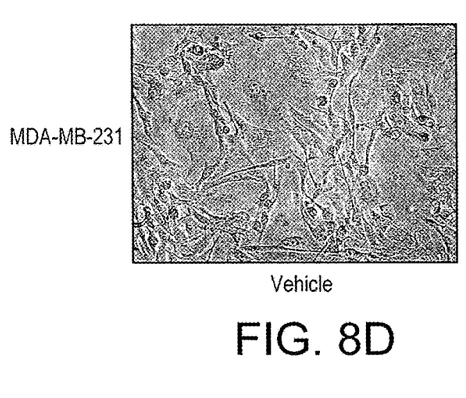
FIGS. 8D, 8E, and 8F show images of cytotoxic and morphological changes in MDA-MB-231 cancer cells treated with compound 3. Cells were treated with the vehicle (DMSO) and different doses of compound 3 for 48 hours. Images were captured by a phase contrast microscope (Leica, Germany), (Magnification: 200×).
Figure 8E:
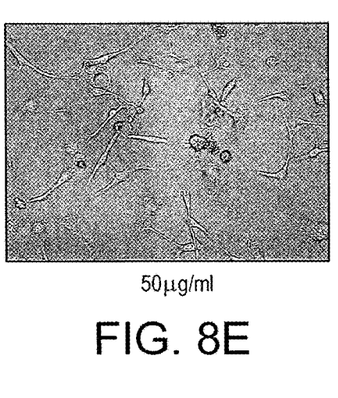
Figure 8F:
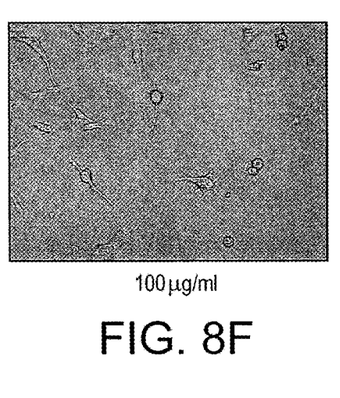

The effect of compound 3 on cell survival was determined using three different cancer cell lines, colon cancer cell (LoVo), liver cancer cells (HepG2), and breast adenocarcinoma cells (MDA-MB-231) as model. The dose responsive curves for compound 3 against the LoVo, HepG2, and MDA-MB-231 cells are summarized in FIG. 6. The $IC_{50}$ values (the concentration of test compound 3 that inhibits 50% of the cell growth), reported in (μg/mL), are summarized in Table 4.

TABLE 4

$IC_{50}$ values for compound 3 with cancer cells

| Cell Type | $IC_{50}$ (μg/mL) |
|---|---|
| LoVo Colon cancer cells | 37.5 |
| HepG2 Liver cancer cells | 38 |
| MDA-MB-231 Breast Cancer cells | 45 |

As confirmed by the data set forth herein, the present inventors have demonstrated that compound 3 displays cytotoxic activity against three different cancer cells. MTT and LDH assays are two tests widely used for in vitro toxicology studies. In general, in order to increase the reliability of the results obtained, more than one assay should be used to determine cell viability in vitro studies.

MTT and LDH assays were used to evaluate the cytotoxic effect of compound 3 against Hepg2, LoVo, and MDA-MB- 231 cell lines to determine anticancer potential. Compound 3 showed strong growth inhibition activity against all three tested human tumor cells, with $IC_{50}$ concentrations ranging from 37.5 to 45 μg/ml. Compound 3 also displayed cytotoxic effects against different tumor cell lines, and was more active against LoVo colon cancer cells (FIGS. 7 and 8A-8F). These results suggest the antitumor activity of compound 3 may be related to the specific new functional group and chemical structure.

The enaminone-grafted trithiocarbonate derivative can be administered by any conventional route of administration, including, but not limited to, intravenous, oral, subcutaneous, intramuscular, intradermal and parenteral. Depending on the route of administration, the enaminone-grafted trithiocarbonate derivative can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

Also provided is a pharmaceutical composition including an enaminone-grafted trithiocarbonate derivative. To prepare the pharmaceutical composition, one or more enaminone-grafted trithiocarbonate derivative compounds or salt thereof, as the active ingredient, is intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

A therapeutically effective amount of the enaminone-grafted trithiocarbonate derivative or an amount effective to treat a disease may be determined initially from in vitro assays described herein and adjusted for specific desired compounds using routine methods.

The following examples are provided by way of illustration.

Example 1

Synthesis of (Z)-ethyl 3-(dimethylamino)-2-(((((Z)-1-(dimethylamino)-3-ethoxy-3-oxoprop-1-en-2-yl) thio)carbonothioyl)thio)acrylate (Compound 3)

A mixture of compound 1 (diethyl 2,2'-(thiocarbonylbis (sulfanediyl))diacetate) (1 g, 3.5 mmol) and DMF-DMA (5 mL) was fused at 100° C. for 1 hour, then allowed to cool at room temperature overnight to afford compound 3 as a crystal.

The resulting compound 3 had the following characteristics: Yield: 70%; m. p. 156° C.; IR (KBr, $cm^{-1}$) v=2974, 2911, 2820, 1686, 1613, 1475, 1430, 1405, 1388, 1331, 1261, 1126, 1092, 1042, 840, 763, 524; $^1$H-NMR (500 MHz, DMSO)=1.05 (t, 7, 6H, $OCH_2$—$CH_3$), 3.11 (S, 3H, N—$CH_3$), 3.13 (S, 3H, N—$CH_3$), 3.28 (s, 6H, —N—$(CH_3)_2$) 3.94 (q, 4H, J=7 Hz, —O—$CH_2$—$CH_3$); 8.01 (S, 2H, N—CH=C); $^{13}$C-NMR (125 MHz, DMSO)=14.99, 60.14, 81.85, 156.04, 167.4, 233.39; MS (DART): Calcd. For $C_{15}H_{25}N_2O_4S_3$ $[M+H]^+$ 393.10065 found 393.09764, Calcd. For $C_{14}^{13}CH_{25}N_2O_4S_3$ 394.10237, $[M+2H]^+$ found 394.10100, Calcd. For $C_{15}H_{25}N_2O_4S_2^{34}S$, $[M+3H]^+$ 395.09388 found 395.09344.

Example 2

Single-Crystal X-Ray Diffraction of Compound 3

SHELXT was used to solve the structure. Data were collected on a Bruker APEX-II D8 Venture area diffractometer, equipped with graphite monochromatic Cu Kα radiation, λ=1.54178 Å at 293 (2) K. Cell refinement and data reduction were carried out by Bruker SAINT. The final refinement was carried out by full-matrix least-squares techniques with anisotropic thermal data for nonhydrogen atoms on F. The supplementary crystallographic data for compound 3 and can be obtained free of charge from CCDC 1542020 at the Cambridge Crystallographic Data Centre.

Example 3

In Vitro Antimicrobial Activity

Biological activity of compound 3 as antimicrobial agents was performed according to (Lam et al. 2016). Lyophilized cultures of *Streptococcus nutans* ATCC 35668, *Bacillus subtilis* and *Brevibacillus laterosporus* Wild strains (Gram positive bacteria), *Salmonella typhi* Wild strain (Gram negative bacteria), Candid *albicans* ATCC 60193 (yeast), *Cryptococcus neoformans* Wild strain (yeast), *Aspergillus fumigatus* AUMC 8794 (mold), and *Penicillium chrysogenum* AUMC (mold) were grown aerobically on the appropriate medium and in incubating conditions before minimal inhibitory, minimal Bactericidal, and minimal fungicidal concentration testing (MIC, MBC, and MFC). The nutrient broth (Oxoid, UK) and potato dextrose broth (Sigma-Aldrich, US) were used to cultivate the bacteria and fungi, respectively.

The total count of microbes was counted by measurement of bacterial and yeast cells; and spores of mold using hemocytometer and account at 400×.

The bacterial suspensions were prepared from bacterial cultures which gave an optical density reading of ~0.9 at 620 nm. The dilution of bacterial cultures was performed using sterile 0.85% NaCl solution to obtain $3 \times 10^6$ cells/ml in sterile nutrient broth. The fungi were cultivated on potato dextrose agar (PDA) at 28° C. for 7 days, and then the spores were harvested from the surface by sterile 0.85% NaCl solution using a Pasteur pipette. The hypae were removed by filtration with a Whatman filter (Pore size, 8 μm) then the inoculum sizes were adjusted to $4 \times 10^6$ CFU/ml.

Compound 3 was diluted in nutrient broth (for bacteria) and RPMI (for fungi) to obtain a desired range of concentrations and a final volume of 100 μl in each well of a 96-well plate which also received 100 μl of diluted microbial suspensions. The fungal microdilution plates were incubated at 28±3° C. for 4 days, whereas the bacterial plates were inoculated at 37±3° C. for 24 hours. A sterile medium alone, and one with inoculum suspension alone, were applied as sterile and growth control. After the incubation, 100 μl of each well were cultivated on nutrient agar (for bacteria) and PDA (for fungi), and then the microbial growth was observed. No microbial growth was used to indicate the MBC and MFC.

To determine MIC of the compound 3, a Mueller-Hinton broth and Potato dextrose broth were used for bacteria and fungi, respectively. The test was performed according to two-fold microdilution assay. Compound 3 was dissolved in sterile culture broth to obtain 6.6 mg of compound 3 per mL of the broth. Two-fold serial dilutions were carried out to obtain concentrations ranging from 3.3-0.05 mg/mL, followed by adding 95 μL of each dilution per well in 96-well plates, and then each well was inoculated with 5 μL of inoculation microbial suspension ($5\times10^8$ colony form unit (CFU)/ml). The plates were incubated at suitable conditions according to the tested microorganism. After incubation, the microbial growth was detected in the wells by p-iodonitrotetrazolium violet (Sigma, USA) reagent. Each well received 20 μL of reagent (0.5 mg/ml) and was then incubated at $37\pm1°$ C. for 30 minutes. A violet color indicated microbial growth in the well. The minimal inhibitory concentration (mg/ml) of compound 3 was estimated as the lowest concentration that inhibited microbial growth. Data are expressed as mean±s.d. of the biological replicates and statistically analyzed using One-Way ANOVA analysis using Tukey test (P<0.05) (SPSS, 13.0).

Example 4

Antiproliferative Activity

HepG2 (human hepatocarcinoma), LoVo (human colorectal adenocarcinoma) and MDA-MB-231 (human breast cancer) cancer cell lines were selected for the in vitro antiproliferative activity. Cells were seeded in 24-well plates at a density of 50,000 cells/well for 24 hours for adherent. After 24 hours, cells were treated with increasing concentrations of compound 3 or an equal volume of vehicle (DMSO) as a control and were incubated for 48 hours. 100 μL of MTT reagent (5 mg/ml) were added. The plates were incubated for 2 hours and absorbance was determined at 540 nm in an ELISA plate reader (Thermo, USA). Percentages of cell survival were calculated as follows: % cell survival=(absorbance of treated cells/absorbance of cells with vehicle solvent)×100. The 50% inhibitory concentration (IC50) was calculated from the dose-response curve obtained by plotting the percentage of cell survival versus the concentration of compound 3.

Lactate dehydrogenase (LDH) assay was performed to assess the LDH release into the media following compound 3 treatments (IC50) on HepG2, LoVo and MDA-MB-231 cells after 48 hours of incubation. LDH cytotoxicity assay was carried out using an in vitro toxicology assay kit (Sigma Aldrich Inc., USA), according to protocol in the user's manual. The amount of LDH released in culture media was measured at 490 nm using an ELISA plate reader (Thermo, USA).

LoVo and MDA-MB-231 cells were grown in 12-well plates and treated with different concentrations of compound 3 for 48 hours. The morphological changes were observed under light inverted microscope attached to a Leica MC-170 HD camera.

It is to be understood that the enaminone-grafted trithiocarbonate derivative is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A compound having the formula:

or a pharmaceutically acceptable salt thereof.

2. A pharmaceutical composition, comprising the compound according to claim 1 and a pharmaceutically acceptable carrier.

3. A method of treating a disease, comprising:
administering to a patient a therapeutically effective amount of the pharmaceutical composition according to claim 2, wherein the disease is cancer and the cancer is selected from the group consisting of liver cancer, colon cancer, and breast cancer or the disease is a fungal infection.

4. The method of claim 3, wherein the fungal infection is caused by a yeast or mold.

5. The method of claim 4, wherein the yeast or mold is *Candida albicans*.

6. The method of claim 4, wherein the yeast or mold is *Cryptococcus neoformans*.

7. The method of claim 4, where the yeast or mold is *Aspergillus fumigatus*.

8. The method of claim 4, where the yeast or mold is *Penicillium chrysogenum*.

9. The method of claim 3, wherein the disease fungal infection is caused by a bacteria.

10. The method of claim 9, wherein the bacteria is *Streptococcus mutans*.

11. The method of claim 9, wherein the bacteria is *Salmonella typhi*.

12. A method of synthesizing a compound, comprising:
mixing diethyl 2,2'-(thiocarbonylbis(sulfanediyl))diacetate with N,N'-dimethylformamide dimethyl acetal to form a mixture; and
heating the mixture to at least about 100° C. for at least about one hour to form a heated mixture including the compound having the structure:

13. The method of claim 12, further comprising:
allowing the heated mixture to cool to room temperature to form a cooled mixture;
maintaining the cooled mixture for at least about 8-10 hours to form a maintained mixture; and
isolating the compound from the maintained mixture.

14. The method of claim 13, wherein the compound is in crystal form.

15. The method of claim 12, further comprising a preliminary step of reacting ethyl cyanoacetate, carbon disulfide (CS2), and ethyl 2-chloroacetate to synthesize the diethyl 2,2'-(thiocarbonylbis(sulfanediyl))diacetate.

\* \* \* \* \*